(12) United States Patent
Desikan et al.

(10) Patent No.: US 6,486,339 B2
(45) Date of Patent: Nov. 26, 2002

(54) PHOSPHORYLATED PRODUCT MADE BY HEATING ALKYLATED PHENOL IN PRESENCE OF SOLID ACID CATALYST

(75) Inventors: Anantha N. Desikan, Ossining, NY (US); George E. Whitwell, Cornwall-on-Hudson, NY (US)

(73) Assignee: Akzo Nobel NV (NL)

( * ) Notice: Subject to any disclaimer, the term of this patent is extended or adjusted under 35 U.S.C. 154(b) by 0 days.

(21) Appl. No.: 09/843,431

(22) Filed: Apr. 26, 2001

(65) Prior Publication Data

US 2001/0025126 A1 Sep. 27, 2001

Related U.S. Application Data

(62) Division of application No. 09/241,911, filed on Feb. 2, 1999.

(51) Int. Cl.$^7$ .............................. C07C 9/12; C07C 9/08
(52) U.S. Cl. .................... 558/92; 558/114; 558/210; 558/211
(58) Field of Search ................ 558/211, 210, 558/114, 92

(56) References Cited

U.S. PATENT DOCUMENTS

| | | | | |
|---|---|---|---|---|
| 2,473,612 A | * | 6/1949 | Shuman ................. 558/211 |
| 3,125,529 A | * | 3/1964 | Simmons et al. ....... 558/211 X |
| 3,655,780 A | | 4/1972 | Kohn et al. ............ 260/624 E |
| 3,859,395 A | * | 1/1975 | Terhune et al. ........ 558/211 |
| 3,968,173 A | | 7/1976 | Klein et al. ............. 260/626 T |
| 3,992,455 A | | 11/1976 | Leston ................... 260/619 R |
| 4,103,096 A | | 7/1978 | Giolito et al. .......... 568/783 |
| 4,197,413 A | | 4/1980 | Kaeding et al. ........ 568/798 |
| 4,283,571 A | | 8/1981 | Keim et al. ............ 568/783 |
| 4,391,998 A | | 7/1983 | Wu et al. ............... 568/781 |
| 4,394,300 A | | 7/1983 | Chu et al. .............. 252/455 Z |
| 4,405,818 A | | 9/1983 | Stead et al. ............ 568/781 |
| 4,484,011 A | | 11/1984 | Van Sickle ............. 568/781 |
| 4,503,269 A | | 3/1985 | Engel et al. ............ 568/783 |
| 4,526,917 A | * | 7/1985 | Axelrod ................. 524/121 |
| 4,532,368 A | | 7/1985 | Swanson et al. ....... 568/791 |
| 4,538,008 A | | 8/1985 | Firth et al. ............. 568/783 |
| 4,547,606 A | | 10/1985 | Olah ...................... 585/477 |
| 4,691,063 A | | 9/1987 | Engel et al. ............ 568/783 |
| 4,792,633 A | | 12/1988 | Wojtkowski ........... 568/46 |
| 5,001,281 A | | 3/1991 | Li .......................... 568/727 |
| 5,015,785 A | | 5/1991 | Steck et al. ............ 568/783 |
| 5,175,375 A | | 12/1992 | Chang ................... 568/781 |
| 5,300,703 A | | 4/1994 | Knifton ................. 568/794 |
| 5,824,622 A | | 10/1998 | Harmer et al. ......... 502/407 |
| 6,242,631 B1 | * | 6/2001 | Hombek et al. ....... 558/211 |

FOREIGN PATENT DOCUMENTS

| | | | |
|---|---|---|---|
| EP | 534019 | 3/1993 | ........ C07C/37/00 |
| GB | 748269 | 4/1956 | |
| GB | 969237 | 9/1964 | |
| GB | 1130997 | 10/1968 | ........ C07C/39/06 |
| GB | 1300877 | 5/1972 | ........ C07C/39/06 |
| GB | 1290103 | 9/1972 | ........ C07C/39/06 |
| JP | 135944/78 | 11/1978 | |

OTHER PUBLICATIONS

Chemical Abstracta, vol. 127, 81242 (1997).
Abstract of JP05032574 (1993).
Derwent Abstract No. 02882B/02 (1978), abstracting J5 3135–944.
I. Pigman et al., "Silica–Alumina Catalyzed Isomerization–Disproportionation of Cresols and Xylenols", J. Amer. Chem. Soc., vol. 76, 6169–6171 (1954).
F. E. Imbert et al., "Cresol Isomerization on HZSM–5", J. of Catalysis 172, 307–313 (1997).

* cited by examiner

Primary Examiner—Floyd D. Higel
Assistant Examiner—Andrea D. Small
(74) Attorney, Agent, or Firm—Richard P. Fennelly

(57) ABSTRACT

The isomerization of an alkylated phenol composition that contains an ortho-alkyl substituted phenol component to isomerize and reduce the level of ortho-alkyl substituted phenol component therein can be accomplished by heating that composition in the presence of a catalytically effective amount of a solid acid catalyst to carry out such isomerization and reduction in the level of ortho-alkyl substituted phenol. Examples of suitable solid acid catalysts can be selected from the H-form zeolites, the supported sulfonic acids, and the heteropoly acids. The resulting isomerized product can be subsequently phosphorylated.

5 Claims, No Drawings

PHOSPHORYLATED PRODUCT MADE BY HEATING ALKYLATED PHENOL IN PRESENCE OF SOLID ACID CATALYST

This application is a divisional of U.S. Ser. No. 09/241,911, filed Feb. 2, 1999.

BACKGROUND OF THE INVENTION

The present invention relates to the isomerization of an alkylation product, formed by the alkylation of phenol with an olefin in the presence of a super acid catalyst containing Bronsted acid functionality. The term "isomerization, as used herein, is meant to indicate the change in overall isomer distribution of an alkylated phenol composition by intra- and/or intermolecular mechanism(s). Such a product normally contains a certain level of undesired mono, di and tri-substituted ortho-alkylphenols (or mixture thereof). It is desired to reduce the level of such ortho-substituted alkylphenols, in such an alkylation product since such ortho-substituted components are significantly less reactive in any later desired phosphorylation reaction using the alkylated phenol and also may be deemed by some persons to be more undesired from a toxicological viewpoint. The phosphorylation of such materials is a well-known reaction and involves treating them with a phosphorylating reagent (such as phosphorus oxytrichloride) at moderately elevated temperature (such as about 100° C. to about 200° C.), preferably in the presence of a Friedel-Crafts catalyst.

One prior art reference that relates to the use of trifluoromethane sulfonic acid (also termed "triflic acid") as the catalyst to achieve the general type of isomerization that forms the subject matter of the present invention is U.S. Pat. No. 4,103,096 to S. L. Giolito et al., which is incorporated herein in its entirety. This patent illustrates, in general terms, one conventional way in which this isomerization reaction has been practiced.

While the use of trifluoromethane sulfonic acid catalyst, as just described, has been utilized commercially, its use is attendant with certain disadvantages. The use of relatively high levels of this catalyst (e.g., 800 to 1000 ppm) may be needed for the desired level of isomerization to take place, and the use of such levels of this acid can cause unacceptable color change in the product of the reaction. Trifluoromethane sulfonic acid is a strong acid that can cause corrosion damage in the process equipment that is used. This catalyst cannot be recovered and hence the catalyst costs are not trivial. Finally, the isomerization reaction using this acid is rather slow (e.g., 40 to 60 hours) in order to reach the target isomer distribution.

Other methods which have been proposed for practicing analogous isomerization reactions are shown in the following patent and literature references: Japanese Patent Publication No. 45-30091/1970; U.S. Pat. No. 3,014,079; and J. Org. Chem., 38, 1929 (1973).

SUMMARY OF THE INVENTION

The present invention relates to the isomerization of the previously described alkylation product to reduce the level of ortho-substituted product therein using a new class of catalyst: a solid acid catalyst.

DESCRIPTION OF THE PREFERRED EMBODIMENTS

As previously described, the present invention is an isomerization reaction which relies upon the use of a novel class of catalyst for that particular type of reaction. In general terms, the alkylation product which is treated herein will comprise a mixture of alkylated phenols: from about 10% to about 30%, by weight of the ortho-substituted alkylated phenols; from about 0% to about 5%, by weight of meta-substituted alkylated phenols; from about 5% to about 15%, by weight of para-substituted alkylated phenols; from 2% to 10% by weight 2,6-dialkylated phenol; and from 1% to 5% tri-alkylated phenol. The present invention relies upon a solid acid catalyst, as will be described below in further detail, to lower the amount of such ortho-substituted species so that the final product preferably has the following composition: from about 10% to about 20%, by weight of ortho-substituted alkylated phenols; from about 5% to about 20%, by weight of meta-substituted alkylated phenols; from about 10% to about 30%, by weight of para-substituted alkylated phenols; and from about 0.5% to 3% 2,6-diisopropyl phenol. The present invention is useful, for example, in the isomerization of mono-alkylsubstituted phenols, such as monoisopropylphenol, of di-alkylsubstituted phenols, such as 2,6-diisopropylphenol, or mixtures containing such alkylated species. The alkyl group or groups on the phenols which are treated will generally have from about two to about twelve carbon atoms therein, preferably three or four, such as exemplified by the isopropyl and tert-butyl groups.

The general type of isomerization reaction is shown in the aforementioned Giolito et al. patent in which the catalyst is employed at a level of from about 0.01% to about 5%, by weight of the alkylphenol, preferably from about 300 to 3000 ppm, and the reaction temperature for the isomerization reaction will be in the range of from about 170° C. to the reflux temperature of the alkylphenol-containing composition which is treated preferably from about 100° C. to about 250° C. The reaction can be performed advantageously at atmospheric pressure or elevated pressure (e.g., up to about 500 psig). The Present process is practiced in the absence of an alkylating agent, such as an olefin.

In accordance with the present invention, a variety of solid acid catalyst types, which are well known to the person of ordinary skill in the art for other chemical reactions, can be used herein. Included as general types of such solid acid catalysts are the H-form zeolites, the supported sulfonic acids, and the heteropoly acids.

Representative examples of H-form zeolites, which form a well-known class of commercially available materials, which find preferred utility in the present invention are the Y-type zeolites and the beta zeolites. Such materials contain Bronsted acid functionality that is needed in the process of the present invention. The ZSM type and mordenite class of zeolites also can be used, but they have been found to have somewhat lower activity. The zeolites that are used herein preferably have a silica/alumina ratio of from about 5 to about 100, most preferably from about 5 to about 80.

Representative supported sulfur acid catalysts include the sulfonic acid catalysts, sulfated zirconia (commercially available, for example, from MEI Chemicals) and the perfluorinated ionic exchange polymers that are available from DuPont under the trademark NAFION. The latter type of material is described at Col. 2, line 24 to Col. 3, line 47 of U.S. Pat. No. 5,001,281 to S. M. Li, which description is incorporated herein by reference.

A supported heteropoly acid catalyst can also be used in connection with the present invention. The description of these materials that appears at Col. 2, line 46 to Col. 5, line 24, for example, of U.S. Pat. No. 5,300,703 of J. F. Knifton, is incorporated herein as describing such known catalytic materials. The Knifton patent deals with the use of such heteropoly acid materials in the synthesis, rather than in the isomerization, of an alkylphenol composition.

The present invention's catalyst selection has a number of advantages, as compared to the use of the liquid catalyst trifluoromethane sulfonic acid previously described. The use of a solid catalyst precludes the possibility that it will become lost by dissolution in the liquid reaction media. There is also no need to use the more difficult means needed to separate a liquid catalyst from a liquid reaction product. The solid acid catalyst is more amenable to a continuous reaction process as compared to the use of a liquid catalyst. The solid catalyst used herein is more easy to regenerate than the trifluoromethane sulfonic acid catalyst that has been previously described. Finally, the solid acid catalysts that are described for use herein have been found to generally yield a product having lower color characteristics than were achieved in many cases using the trifluoromethane sulfonic acid catalyst of the prior art.

When a zeolite is selected as the solid acid catalyst for use herein, it has been found that certain novel compositions can be obtained. Such compositions comprise a mixed alkylphenols wherein the ratio of ortho- to meta- and para- isomers is no more than about 1.0, the amount of 2,6-dialkyl phenol is no more than about 4.0%, by weight of the entire composition, and the amount of trialkyl phenol is from about 4% to about 75% (preferably about 4% to about 15%), by weight of the entire composition.

The present process can be practiced using a variety of reaction schemes. For example, it is possible to implement the present invention using batch reaction, fixed bed reaction, or reactive distillation reaction techniques, or a combination of those techniques.

In those cases where a zeolite catalyst is employed, it has been found that such catalysts undergo varying levels of deactivation, due to the formation of carbonaceous species that block the active sites. Such a catalyst can be easily regenerated using known regeneration procedures. For example, a controlled burnout of the carbonaceous species can be achieved using air/nitrogen mixtures that are lean in oxygen at temperatures of from about 200° C. to about 500° C.

The invention will be further illustrated in the following non-limiting Examples.

EXAMPLES

Isomerization reactions were carried out using catalysts both in a fixed bed reactor and in a stirred batch reactor. Tests using the fixed bed reactor were carried out at the desired temperatures (150–250° C.) and pressures (atmospheric to 150 psig). Catalysts used were powders or crushed particles in a narrow mesh range or commercial extrudates. Alkylated phenol was pumped into the reactor as a liquid and was heated to about 180° C. before contacting the catalyst. Nitrogen was used sometimes as an inert carrier gas. The reactants were fed into the top of the catalyst bed. Liquid isomerized phenol was collected in a gas/liquid separator, and the liquid samples were analyzed with a gas chromatograph, using a flame ionization detector. The results reported are in GC area % and can be converted into the wt % by using the appropriate response factors. Catalysts were pretreated in situ as needed prior to the isomerization reaction.

EXAMPLE 1

This Example illustrates the isomerization of alkyated phenol using a $SO_4/ZrO_2$ catalyst.

2.0 gm of $SO_4/ZrO_2$ extrudates obtained from Magnesium Elektron Limited, was loaded into a stainless steel reactor and was calcined in dry air at 600° C.–650° C. for two hours. The catalyst was then brought to 180° C. and the system was purged with a $N_2$ stream prior to the isomerization reaction. The results of the isomerization are summarized in the Table given below:

TABLE 1

| Day | | 1.0 | 1.0 | 1.0 | 2.0 | 2.0 |
|---|---|---|---|---|---|---|
| Time/Hr | 0 (Feed) | 2.0 | 3.0 | 5.0 | 6.3 | 8.5 |
| Liquid Rate/ml min$^{-1}$ | | 0.1 | 0.1 | 0.1 | 0.1 | 0.1 |
| LHSV/Hr$^{-1}$ | | 3.0 | 3.0 | 3.0 | 3.0 | 3.0 |
| Temperature/° C. | | 185.0 | 185.0 | 185.0 | 185.0 | 185.0 |
| Phenol/GC Area % | 55.88 | 58.19 | 55.41 | 55.16 | 54.68 | 53.65 |
| o-ipp/GC Area % | 23.11 | 15.82 | 17.45 | 17.70 | 16.65 | 18.13 |
| m,p-ipp/GC Area % | 9.19 | 19.27 | 19.55 | 19.06 | 17.96 | 18.75 |
| 2,6 di-ipp/GC Area % | 4.48 | 0.84 | 1.14 | 1.23 | 1.39 | 1.57 |
| 2,4 di-ipp/GC Area % | 4.88 | 3.49 | 4.11 | 4.48 | 5.70 | 5.36 |
| 2,5 di-ipp/GC Area % | 0.85 | 1.16 | 1.17 | 1.21 | 1.71 | 1.29 |
| 3,5 di-ipp/GC Area % | | 0.87 | 0.77 | 0.71 | 1.00 | 0.53 |
| tri-ipp/GC Area % | 1.62 | 0.00 | 0.41 | 0.45 | 0.65 | 0.52 |
| o/p ratio | 2.51 | 0.82 | 0.89 | 0.93 | 0.93 | 0.97 |

EXAMPLE 2

This Example illustrates the isomerization of an alkyated phenol over a beta zeolite catalyst obtained from Zeolyst International (CBV 861E).

First, 2.0 g of beta zeolite pellets was loaded into the stainless steel reactor. The catalyst was used without any pretreatment. The results are summarized in the Table below:

TABLE 2

| Day | | 1 | 1 | 1 | 1 | 1 | 1 | 2 | 2 | 2 | 3 |
|---|---|---|---|---|---|---|---|---|---|---|---|
| Time/Hr | 0 (Feed) | 0.8 | 1.0 | 1.5 | 3.0 | 5.0 | 7.0 | 9.0 | 10.0 | 12.0 | 18.0 |
| Liquid Flow Rate/ml min$^{-1}$ | | 0.2 | 0.2 | 0.2 | 0.2 | 0.2 | 0.2 | 0.2 | 0.2 | 0.2 | 0.2 |
| LHSV | | 3.0 | 3.0 | 3.0 | 3.0 | 3.0 | 3.0 | 3.0 | 3.0 | 3.0 | 3.0 |
| Temperature/° C. | | 180.0 | 180.0 | 180.0 | 180.0 | 180.0 | 180.0 | 180.0 | 180.0 | 180.0 | 190.0 |
| Phenol/GC Area % | 55.88 | 60.2% | 56.4% | 60.8% | 62.0% | 60.1% | 64.3% | 63.3% | 60.4% | 60.6% | 60.3% |
| o-IPP/GC Area % | 23.11 | 15.3% | 14.2% | 14.6% | 13.4% | 13.9% | 13.9% | 14.3% | 15.0% | 15.4% | 14.1% |
| m,p-IPP/GC Area % | 9.19 | 18.4% | 21.7% | 18.6% | 19.1% | 19.8% | 17.0% | 16.9% | 18.3% | 17.1% | 19.4% |
| 2,6 di-ipp/GC Area % | 4.48 | 0.8% | 0.9% | 1.4% | 1.3% | 1.5% | 1.3% | 1.5% | 1.7% | 1.9% | 1.7% |
| 2,4 di-ipp/GC Area % | 4.88 | 1.7% | 2.0% | 2.1% | 2.0% | 2.1% | 1.6% | 1.9% | 2.0% | 2.4% | 2.0% |
| 2,5 di-ipp/GC Area % | 0.85 | 1.8% | 2.2% | 1.7% | 1.6% | 1.8% | 1.3% | 1.5% | 1.7% | 1.8% | 1.7% |
| 3,5 di-IPP/GC Area % | | 1.3% | 1.9% | 1.0% | 0.9% | 0.9% | 0.6% | 0.6% | 0.7% | 0.7% | 0.9% |
| tri-IPP/GC Area % | 1.62 | 0.4% | 0.7% | 0.7% | 0.7% | 0.8% | 0.6% | 0.6% | 0.8% | 0.8% | 0.8% |
| o/p ratio | 2.51 | 0.83 | 0.66 | 0.78 | 0.70 | 0.70 | 0.82 | 0.85 | 0.82 | 0.90 | 0.73 |

It is clear from the Examples 1–2 described above, that these two types of catalysts are effective for the isomerization of alkylated phenol. They also offer several advantages over the triflic acid-based process: a) the process is non-corrosive, b) catalysts can be separated from the reaction mixture and be reused and hence catalyst costs are more economical, c) no color formation is observed, as compared to the case of the triflic acid catalyzed isomerization process.

EXAMPLE 3

This Example illustrates the isomerization of alkyated phenol on a perfluorinated ion-exchange polymer (NAFION brand from DuPont) on a silica support.

In this Example, about 1.0 gm of the NAFION brand/SiO$_2$ extrudates, was loaded into a stainless steel reactor and dried in a nitrogen gas stream at 150° C. for four hours prior to the evaluation. The catalyst was then brought to 155° C. while in the nitrogen gas stream. Isomerization was carried out at 155° C. and at atmospheric pressure. The results are summarized in Table 3 that follows:

| Day | 1 | 1 | 1 | 1 | 1 | 1 | 1 |
|---|---|---|---|---|---|---|---|
| Time | 0(Feed) | 0:40 | 1:20 | 2:25 | 3:25 | 4:25 | 5:25 | 20:30 |
| LHSV/Hr-1 | | 2.5 | 2.5 | 2.5 | 2.5 | 2.5 | 2.5 | 2.5 |
| Composition/GC Area % | | | | | | | | |
| Phenol | 40.15 | 32.23 | 31.71 | 30.98 | 31.34 | 31.19 | 30.42 | 31.11 |
| o-IPP | 27.50 | 16.92 | 16.12 | 14.40 | 15.27 | 16.43 | 16.48 | 20.41 |
| m,p-ipp | 8.92 | 28.70 | 30.31 | 31.96 | 31.26 | 29.85 | 29.39 | 24.14 |
| 2,6 | 7.36 | 2.03 | 1.17 | 0.93 | 1.03 | 1.18 | 1.23 | 1.95 |
| 2,4 | 8.99 | 6.71 | 6.16 | 5.38 | 5.81 | 6.37 | 6.59 | 8.56 |
| 2,5 | 1.38 | 4.25 | 4.50 | 4.46 | 4.49 | 4.56 | 4.67 | 4.88 |
| 3,5 | | 5.94 | 6.25 | 7.27 | 7.02 | 6.60 | 6.67 | 5.16 |
| tri | 4.80 | 2.48 | 2.40 | 2.24 | 2.30 | 2.55 | 2.69 | 3.34 |
| o/m,p ratio | 3.08 | 0.59 | 0.53 | 0.45 | 0.49 | 0.55 | 0.56 | 0.85 |

EXAMPLE 5

Another HY Zeolite (Zeolyst CBV 600-Si/Al ratio: 5.2) was used as 14–30 mesh size particles for the isomerization reaction. Table 5 summarizes the results obtained in this test.

TABLE 3

Isomerization activity of Nafion/SiO$_2$ composite catalysts at 155° C.

| Day | | 1 | 1 | 1 | 2 | 2 | 2 | 3(2) | 3 | 3 | 3 | 4(3) | 4 | 5 | 5 | 5 |
|---|---|---|---|---|---|---|---|---|---|---|---|---|---|---|---|---|
| Time/Hr | 0.0 | 0.75 | 2.5 | 4.5 | 8 | 12 | 14 | 30 | 35 | 38 | 39 | 56 | 59 | 65 | 67 | 82.5 |
| Liquid Rate(ml/min) | | 0.05 | 0.1 | 0.1 | 0.1 | 0.1 | 0.05 | 0.05 | 0.05 | 0.1 | 0.05 | 0.05 | 0.1 | 0.05 | 0.05 | 0.05 |
| LHSV(Hr$^{-1}$) | | 1.5 | 3 | 3 | 3 | 3 | 1.5 | 1.5 | 1.5 | 3 | 1.5 | 1.5 | 3 | 1.5 | 1.5 | 1.5 |
| Temperature (° C.) | | 155 | 155 | 155 | 155 | 155 | 155 | 155 | 155 | 155 | 155 | 155 | 155 | 155 | 140 | 155 |
| Carrier Gas | | N2 | N2 | N2 | N2 | N2 | N2 | N2 | N2 | N2 | N2 | N2 | N2 | N2 | N2 | N2 |
| Phenol (GC%) | 55.88 | 69.67 | 55.62 | 55.84 | 52.07 | 55.4 | 57.04 | 52.6 | 54.45 | 52.16 | 59.67 | 53.34 | 49.9 | 59.05 | 59.29 | 52.7 |
| o-ipp (GC%) | 23.11 | 12.69 | 20.07 | 20.62 | 20.18 | 20.68 | 19.3 | 18.61 | 18.59 | 20.95 | 19.84 | 18.86 | 22.5 | 17.54 | 18.7 | 18.9 |
| m,p-ipp (GC%) | 9.19 | 11.07 | 15.8 | 15.12 | 16.5 | 15.17 | 16.08 | 19 | 17.78 | 16.54 | 13.39 | 18.39 | 17.6 | 15.89 | 14.9 | 18.3 |
| 2,6 di-ipp (GC%) | | | | | | | | | | | | | | | | |
| 2,4 di-ipp (GC%) | 4.88 | 2.39 | 4.83 | 4.71 | 6.18 | 4.78 | 4.49 | 5.9 | 5.45 | 5.64 | 3.79 | 5.64 | 5.81 | 3.74 | 3.8 | 5.9 |
| 2,5 di-ipp (GC%) | 0.85 | 0.71 | 0.89 | 0.87 | 1.34 | 0.84 | 0.86 | 1.18 | 1.09 | 1.01 | 0.71 | 1.09 | 1.09 | 0.87 | 0.74 | 1.1 |
| 3,5 di-ipp (GC%) | | 0.96 | 0 | | 0.49 | | | 0.47 | 0.42 | 0 | | 0.37 | 0.2 | 0.78 | 0.15 | 0.36 |

It is clear from the results obtained that at relatively mild temperatures, the catalyst was quite active for the isomerization of phenol. Liquid hourly space velocities (LHSV) has an effect on the isomerization activity, but it is noteworthy that the catalyst was remarkably stable for an extended period.

EXAMPLE 4

Zeolite type Y is also effective, as shown herein, at catalyzing the isomerization of ortho-substituted isopropylphenols to more stable isomers and for the isomerization of 2,6-di-isopropyl phenol. HY Zeolite obtained from Zeolyst International (CBV 712 Si/Al ratio 12) was used as 14–30 mesh size particles. The following Table summarizes the results.

The catalyst is found to be effective for the isomerization of ortho-isopropyl phenol and 2,6-di-isopropyl phenols:

| Time | | 2:00 | 4:00 | 6:00 | 7:00 | 23:00 | 24:02 |
|---|---|---|---|---|---|---|---|
| Day | | 1 | 1 | 1 | 1 | 1 | 1 |
| LHSV/Hr-1 | | 1 | 1 | 1 | 1 | 1 | 1 |
| Component/GC Area % | | | | | | | |
| Phenol | 40.15 | 41.82 | 39.54 | 38.93 | 39.16 | 34.44 | 37.53 |
| o-IPP | 27.50 | 13.87 | 13.80 | 15.15 | 15.64 | 16.49 | 19.05 |
| m,p-IPP | 8.92 | 26.97 | 28.99 | 28.22 | 27.50 | 29.48 | 24.59 |
| 2-6-diisopropyl | 7.36 | 1.15 | 0.69 | 0.74 | 0.80 | 0.90 | 1.22 |
| 2,4-di-IPP | 8.99 | 3.33 | 3.27 | 3.65 | 3.83 | 4.31 | 5.00 |
| 2,5-di-IPP | 1.38 | 2.47 | 2.91 | 3.18 | 3.28 | 3.67 | 3.63 |
| 3,5-di-IPP | | 3.69 | 4.42 | 4.59 | 4.59 | 5.10 | 4.13 |
| tri | 4.80 | 2.55 | 2.87 | 3.19 | 3.24 | 3.62 | 3.72 |
| o/p ratio | 3.08 | 0.51 | 0.48 | 0.54 | 0.57 | 0.56 | 0.77 |

EXAMPLE 6

HY Zeolite (Zeolyst CBV 780-Si/Al:80) was used as described in the previous example and also found to be effective for the isomerization reaction. The following Table summarizes the results:

| Time | 2:00 | 3:00 | 4:00 | 6:00 | 7:00 | 19:40 | 23:30 |
|---|---|---|---|---|---|---|---|
| Day | 1 | 1 | 1 | 1 | 1 | 1 | 1 |
| LHSV/Hr-1 | 1 | 1 | 1 | 1 | 1 | 1 | 1 |
| Temperature/° C. | 220 | 220 | 220 | 220 | 220 | 220 | 220 |
| Component/GC Area % | | | | | | | |
| Phenol | 40.26 | 33.06 | 32.68 | 34.33 | 37.26 | 37.71 | 38.44 | 38.83 |
| o-IPP | 27.46 | 19.56 | 19.94 | 20.87 | 22.39 | 23.01 | 24.02 | 23.89 |
| m,p-IPP | 8.95 | 25.53 | 24.94 | 23.97 | 21.71 | 20.82 | 19.27 | 19.44 |
| 2,6 | 7.30 | 1.70 | 1.80 | 1.85 | 1.89 | 1.98 | 2.15 | 2.09 |
| 2,4 | 8.96 | 7.46 | 7.86 | 7.82 | 7.50 | 7.49 | 7.64 | 7.41 |
| 2,5 | 1.44 | 4.66 | 4.76 | 4.47 | 3.93 | 3.81 | 3.58 | 3.51 |
| 3,5 |  | 5.38 | 5.30 | 4.53 | 3.45 | 3.11 | 2.50 | 2.44 |
| tri | 4.84 | 1.55 | 1.71 | 1.74 | 1.88 | 2.06 | 2.40 | 2.39 |
| o/p ratio | 3.07 | 0.77 | 0.80 | 0.87 | 1.03 | 1.11 | 1.25 | 1.23 |

EXAMPLE 7

The HY Zeolite brand catalyst, as described in Example 4, was tested at higher pressures to determine the effect of pressure. The results are summarized in the following Table:

| Time/Hrs | 4:00 | 6:00 | 22:00 | 26:00 | 48:00 | 63:30 | 70:00 |
|---|---|---|---|---|---|---|---|
| Day | 1 | 1 | 1 | 2 | 2 | 3 | 3 |
| LHSV/Hr$^{-1}$ | 1 | 1 | 1 | 1 | 1 | 1 | 1 |
| Temperature/° C. | 220 | 220 | 220 | 220 | 220 | 220 | 220 |
| Composition/GC Area % | | | | | | | |
| Phenol | 39.34 | 38.40 | 40.05 | 38.49 | 38.13 | 39.55 | 38.72 | 38.60 |
| o-IPP | 27.35 | 13.38 | 10.93 | 13.61 | 13.96 | 14.93 | 14.20 | 15.21 |
| m,p-IPP | 9.95 | 31.32 | 33.14 | 30.26 | 30.24 | 28.55 | 29.65 | 28.18 |
| 2,6 | 7.30 | 0.88 | 0.53 | 0.88 | 0.92 | 0.93 | 0.81 | 1.08 |
| 2,4 | 9.13 | 4.10 | 3.06 | 4.21 | 4.41 | 4.51 | 4.49 | 4.72 |
| 2,5 | 1.53 | 3.32 | 3.05 | 3.74 | 3.81 | 3.70 | 3.92 | 3.88 |
| 3,5 | 0.00 | 4.32 | 4.80 | 5.13 | 5.09 | 4.41 | 4.83 | 4.73 |
| tri-IPP | 4.73 | 2.62 | 1.93 | 2.65 | 2.72 | 2.76 | 2.92 | 2.81 |
| o/p ratio | 2.75 | 0.43 | 0.33 | 0.45 | 0.46 | 0.52 | 0.48 | 0.54 |

EXAMPLE 8

Commercial HY Zeolite extrudates (Zeolyst CBV 712 XE) were tested in the isomerization reaction of the present invention, both in the crushed and uncrushed forms, to determine its activity for the isomerization reaction. The results are summarized in the following Table:

| Time | 0 Feed | 24:45 | 40:00 | 80:00 | 202:00 | 297:00 | 405:00 | 487:00 |
|---|---|---|---|---|---|---|---|---|
| Day | | 2 | 2 | 3 | 8 | 12 | 17 | 27 |
| LHSV | | 1 | 1 | 1 | 1 | 1 | 1 | 1 |
| Temperature/° C. | | 190 | 190 | 190 | 195 | 200 | 200 | 210 |
| Compostion/GC Area % | | | | | | | | |
| Phenol | 39.34 | 39.03 | 37.68 | 37.80 | 38.25 | 37.69 | 36.36 | 34.69 |
| o-IPP | 27.35 | 23.01 | 20.56 | 19.43 | 18.83 | 17.78 | 18.99 | 20.42 |
| m,p-IPP | 9.95 | 19.48 | 23.18 | 24.15 | 24.36 | 26.44 | 25.18 | 24.10 |
| 2,6 | 7.30 | 3.57 | 2.59 | 2.33 | 1.99 | 1.13 | 1.37 | 1.62 |
| 2,4 | 9.13 | 7.61 | 7.15 | 6.87 | 6.84 | 5.57 | 6.45 | 7.06 |
| 2,5 | 1.53 | 2.33 | 2.98 | 3.20 | 3.51 | 4.08 | 4.25 | 4.46 |
| 3,5 | 0.00 | 1.07 | 1.87 | 2.27 | 2.64 | 4.09 | 3.83 | 3.68 |
| tri-IPP | 4.73 | 3.69 | 3.73 | 3.66 | 3.33 | 3.19 | 3.32 | 3.72 |
| o/p ratio | 2.75 | 1.18 | 0.89 | 0.80 | 0.77 | 0.67 | 0.75 | 0.85 |

EXAMPLE 9

The HY Zeolite extrudates, which are described in Example 8, after about 500 hours on stream were subjected to a rapid deactivation test and were regenerated using air at 450° C. for about 4–6 hours. The regenerated catalyst was tested for its isomerization activity, and the results are summarized in the following Table:

| Time | 21:00 | 43:00 | 73:00 | 100:00 | 212:00 | 241:00 |
|---|---|---|---|---|---|---|
| Day | 1 | 2 | 3 | 4 | 8 | 10 |
| LHSV/Hr$^{-1}$ | 1 | 1 | 1 | 1 | 1 | 1 |
| Temperature/° C. | 190 | 190 | 195 | 195 | 205 | 205 |
| Composition/GC Area % | | | | | | |
| Phenol | 37.74 | 36.96 | 32.09 | 32.63 | 35.94 | 37.51 | 39.53 |

-continued

| | | | | | | | |
|---|---|---|---|---|---|---|---|
| o-IPP | 27.54 | 18.28 | 19.90 | 21.34 | 23.38 | 23.03 | 23.97 |
| m,p-IPP | 10.23 | 25.50 | 25.38 | 22.71 | 18.62 | 19.21 | 17.81 |
| 2,6 | 7.51 | 1.43 | 1.83 | 2.36 | 3.05 | 2.41 | 2.54 |
| 2,4 | 9.35 | 6.33 | 7.81 | 8.66 | 8.61 | 7.67 | 7.41 |
| 2,5 | 1.62 | 4.14 | 4.84 | 4.85 | 4.15 | 4.11 | 3.58 |
| 3,5 | 0.00 | 4.27 | 4.34 | 3.47 | 2.08 | 2.55 | 2.00 |
| tri-IPP | 5.00 | 2.68 | 3.43 | 3.98 | 3.96 | 3.52 | 3.17 |
| o/p ratio | 2.69 | 0.72 | 0.78 | 0.94 | 1.26 | 1.20 | 1.35 |

EXAMPLE 11

In a similar fashion to Example 4, an H-form mordenite (Si/Al ratio: 20 and 30-14 mesh) at 200° C. and LHSV of 1 hr$^{-1}$ gave initial conversion rates of 45% for ortho to meta and para and 70% for 2,6-di-iso-propylphenol to 3,5-di-isopropylphenol and others and, at 210° C. and a LHSV of 2.51 hr$^{-1}$, gave initial conversion rates of 10% for ortho to meta and para and 25% for 2,6-di-iso-propylphenol to 3,5-di-isopropylphenol and others. In both of these cases, the catalyst activity for isomerization was insignificant after twenty-four hours of operation.

EXAMPLE 12

In this Example, 20 gm of SiO$_2$ pellets (Degussa-Support 350 product, surface area: 160 m$^2$g$^{-1}$, pore volume: 0.75 cm$^3$g$^{-1}$) was impregnated with an aqueous solution of silicotungstic acid until incipient wetness. The impregnated support was then dried/calcined in air at 200° C. for three hours prior to use in the reaction. An approximate loading of 30 wt % HPA on the SiO$_2$ was achieved.

Then, 50 gm of alkylated phenol (Table 1) was weighed into a three neck round bottom flask. To this solution was added 5 gm of HPA/SiO$_2$ pellets. The reaction was performed at 175–180° C., with constant stirring with a magnetic stirrer, under reflux conditions. The temperature of the reactant/product mixture was measured with a thermocouple immersed into the liquid. Samples were taken at regular intervals and analysis was done using a gas chromatograph. Results are tabulated in the following Table:

Isomerization of alkylated phenol.
Isomerization performed at 180° C.

| Compound | Gas Chromatograph/wt % | | | | | |
|---|---|---|---|---|---|---|
| Time | 0 min | 10 min | 45 min | 90 min | 140 min | 210 min |
| Phenol | 54.4 | 54.4 | 52.2 | 52.1 | 51.9 | 51.6 |
| o-IPP | 24.6 | 23.4 | 19.9 | 17.4 | 15.2 | 13.5 |
| m,p-IPP | 8.1 | 13.2 | 18.9 | 23.1 | 25.8 | 28.3 |
| 2,6-di-IPP | 3.5 | 2.5 | 1.3 | 0.8 | 0.6 | 0.5 |
| 2,4-di-IPP | 4.9 | 4.7 | 4.3 | 4.1 | 3.8 | 3.5 |
| 2,5-di-IPP | 0.8 | 1.1 | 1.3 | 1.7 | 1.9 | 2.0 |
| 2,4,6-tri-IPP | 1.3 | 0.6 | 0.3 | 0.2 | 0.1 | 0.2 |
| Other tri-IPP | 0.3 | – | 0.1 | 0.2 | 0.1 | 0.1 |
| o/m,p ratio | 3.0 | 1.8 | 0.82 | 0.61 | 0.59 | 0.47 |

EXAMPLE 13

This Example illustrates the phosphorylation of the isomerized product of the present invention. About 120 g of the isomerized product was phosphorylated with about 150 g of phosphorus oxytrichloride in the presence of 0.5 g of magnesium dichloride at atmospheric pressure and a temperature of about 180° C. The phosphorylated sample was stripped under vacuum to remove free phenolics and was washed with oxalic acid and caustic solutions to remove the catalyst. The product was then dried under vacuum for about four hours to reduce the water level in the product to about 100 ppm. The composition of the alkylated phosphate ester was determined to be (in GC area %): phenol: 42.7; o-IPP: 13.6; m,p-IPP: 35.3; 2,6-di-IPP: 0.1; 2,4-di-IPP: 1.4; 2,5- and 3,5-di-IPP: 3.9; 2,3-di-IPP: 0.1; 2,4,6-tri-IPP: 2.6; other tri-IPP: 0.2.

It can be seen from the preceding Examples that the method of this invention enables the effective and efficient preparation of meta- and some para-alkylphenols from other alkylphenol isomers. It is also seen that meta-alkylphenols may be prepared from an olefin and phenol in a single process step using a ZSM-5 zeolite in accordance with the method of this invention. As has been shown, the method of this invention is effective and efficient and requires neither the handling of difficult-to-handle materials such as HF nor the employment of special process steps to remove solid catalyst.

It will thus be seen that the objects set forth above are effectively attained and, since certain changes may be made in the above method without departing from the scope of the invention, it is intended that all matter contained in the above description shall be interpreted as illustrative and not in a limiting sense. The scope of protection desired is set forth in the Claims that follow.

We claim:

1. A process which comprises phosphorylation of a composition comprising ortho-substituted alkylated phenol composition that comprises comprising mono-, 2,6-dialkyl, and tri-substituted phenol species, wherein the alkyl group or groups have from two to about twelve carbon atoms therein, the amount of 2,6-dialkyl phenol is no more than about 4.0%, and the amount of trialkyl phenol is from about 4% to about 75%, by weight of the entire composition, to isomerize and reduce the level of ortho-substituted alkyl phenol component therein in the presence of a catalytically effective amount of a solid acid catalyst to carry out such isomerization and reduction in the level of ortho-substituted alkyl phenol component.

2. A process which comprises the phosphorylation of a composition comprising mixed alkylphenols wherein the ratio of ortho- to meta- and para- isomers is no more than about 1.0, the amount of 2,6-dialkyl phenol is no more than about 4.0%, by weight of the entire composition, wherein the alkyl group or groups have from two to about twelve carbon atoms therein, and the amount of trialkyl phenol is from about 4% to about 75%, by weight of the entire composition.

3. A process as claimed in claim 2 wherein the amount of trialkyl phenol is from about 4% to about 15%, by weight of the entire composition.

4. A process as claimed in claim 2 wherein the alkyl group is isopropyl.

5. A process as claimed in claim 3 wherein the alkyl group is isopropyl.

* * * * *

UNITED STATES PATENT AND TRADEMARK OFFICE
CERTIFICATE OF CORRECTION

PATENT NO. : 6,486,339 B2  Page 1 of 1
DATED : November 26, 2002
INVENTOR(S) : Desikan et al.

It is certified that error appears in the above-identified patent and that said Letters Patent is hereby corrected as shown below:

Column 10,
Line 36, insert -- an -- before "ortho -substituted"
Line 37, delete "comprising" after "comprises"

Signed and Sealed this

Eighteenth Day of March, 2003

JAMES E. ROGAN
*Director of the United States Patent and Trademark Office*